United States Patent [19]

Poppendiek

[11] Patent Number: 5,040,541
[45] Date of Patent: Aug. 20, 1991

[54] WHOLE BODY CALORIMETER

[75] Inventor: Heinz F. Poppendiek, La Jolla, Calif.

[73] Assignee: Thermonetics Corporation, La Jolla, Calif.

[21] Appl. No.: 902,704

[22] Filed: Sep. 2, 1986

Related U.S. Application Data

[63] Continuation-in-part of Ser. No. 718,747, Apr. 1, 1985, abandoned, which is a continuation of Ser. No. 407,737, Aug. 13, 1982, abandoned.

[51] Int. Cl.$^5$ ............................................. A61B 5/08
[52] U.S. Cl. ..................................... 128/718; 374/31
[58] Field of Search .................... 128/113, 736, 265.26, 128/262.12, 702.13, 716, 718; 374/29–42; 9/51

[56] References Cited

U.S. PATENT DOCUMENTS

| | | | |
|---|---|---|---|
| 2,916,033 | 12/1959 | Coleman | 128/718 |
| 2,940,041 | 1/1961 | Burlis et al. | 128/718 |
| 2,984,097 | 5/1981 | Mniazuk et al. | 128/718 |
| 3,045,665 | 7/1962 | Moyat | 128/718 |
| 3,142,983 | 8/1964 | Dudley et al. | 374/29 |
| 3,396,719 | 8/1968 | Taylor et al. | 128/718 |
| 4,386,604 | 6/0783 | Hershey | 128/718 |

FOREIGN PATENT DOCUMENTS 2940518  9/1981  Fed. Rep. of Germany ........ 374/33

OTHER PUBLICATIONS

Benzinger et al. "Human Calorimetry by means of Gradient Principle", J. Applied Phys. vol. 12, Apr. 12, 1958, pp. 51–524.

*Medical Physiology*, ed., Vernon B. Mountcastle, ch. 53, "Energy Exchanger", pp. 1238–1251.

Quattrone, "Improved Gradient Layer Animal Calorimeter", Review of Scientific Instrumentation, vol. 36, No. 6, Jun. 1905, pp. 832–835.

Vadso, "A Micro Calorimeter Ser. Biological Analysis", vol. 21, No. 2–3, pp. 8–21, 1974.

*Primary Examiner*—Randall L. Green
*Assistant Examiner*—K. Reichle
*Attorney, Agent, or Firm*—Frank E. Mauritz

[57] ABSTRACT

A calorimeter box accommodates a person lying on a cot. The system measures metabolic releases.

The person's head extends into a transparent box-shaped duct system. Ambient air flows from the room in which the calorimeter is located into the duct system and past the person's head and neck into the calorimeter box. substantially all convection and evaporative heat losses from the person's head are transported into the calorimeter itself by the air flow. If the air flow were to stop, i.e., failed to exist, the person would have no trouble breathing because in essence his head is in the room. This obviates safety and claustrophobia problems; further the subject can talk to attendants in the room.

The calorimeter is of heavy aluminum panel construction for structural strength and for purposes of providing a heat sink. Coil of tubing remove heat from the aluminum panels, and water of constant temperature is circulated through such tubing to maintain the aluminum panels at a substantially constant temperature. Thermopiles are connected electrically in series to measure or indicate all the heat flowing from the interior of the calorimeter box to the heat sink. In another form of the invention, the subject, which in this instance may be an animal is visible through a transparent vacuum window. New means and techniques are provided for accounting for the heat losses resulting from heat flow through the insulating frame and the window.

11 Claims, 3 Drawing Sheets

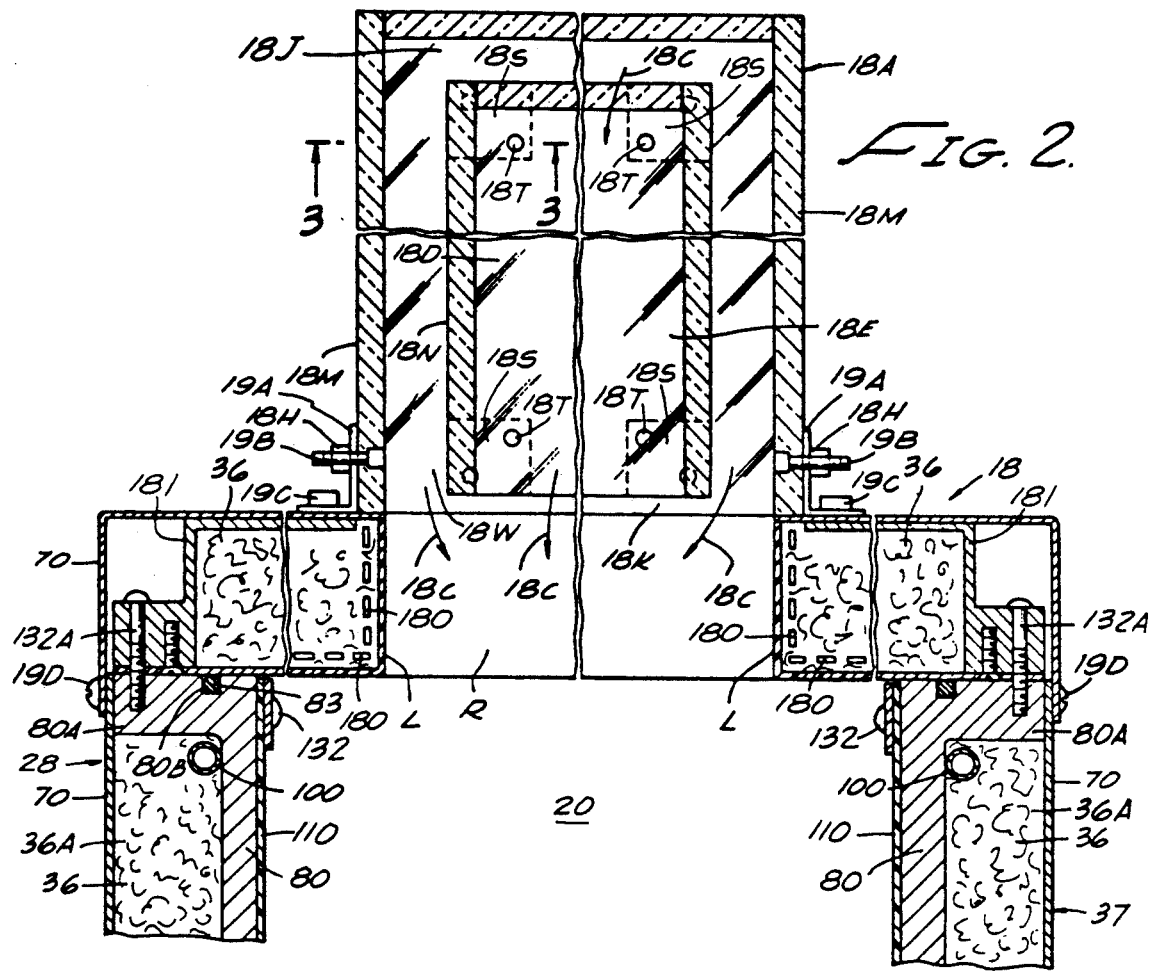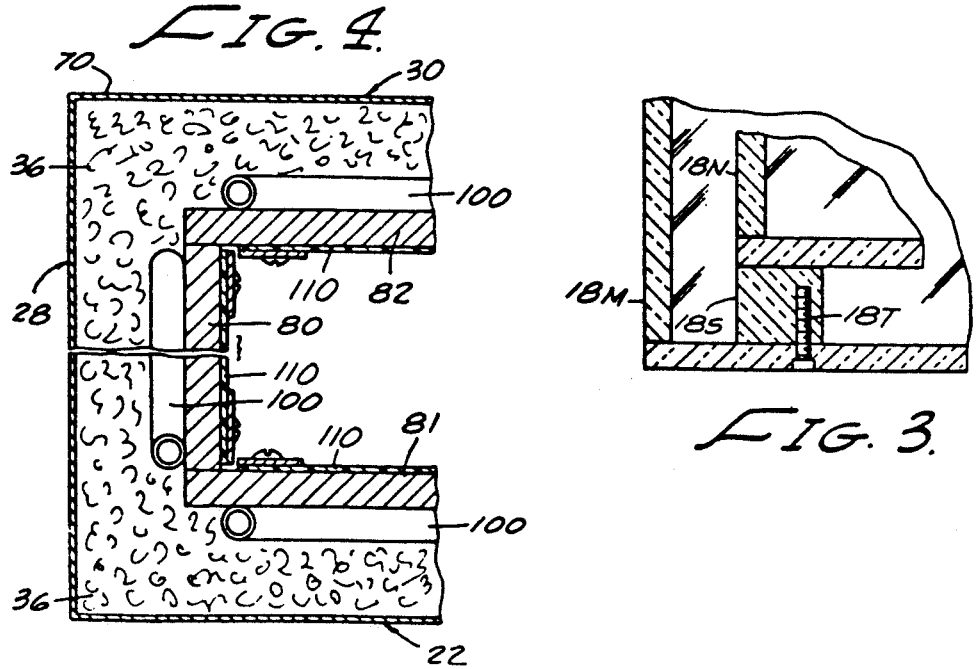

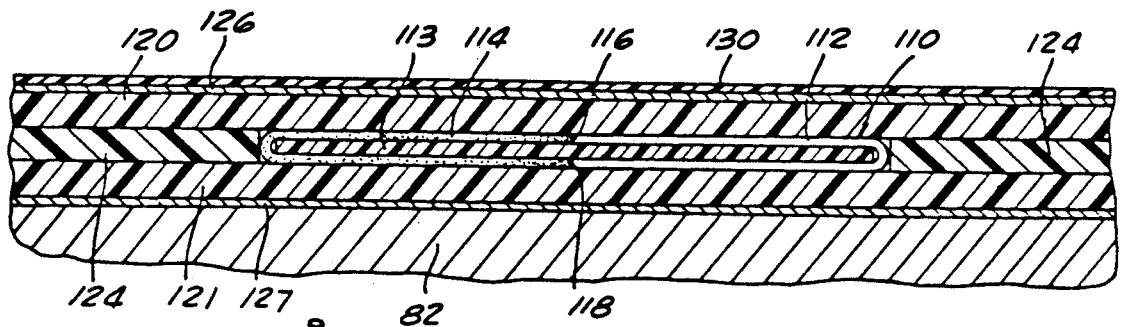
FIG. 6.
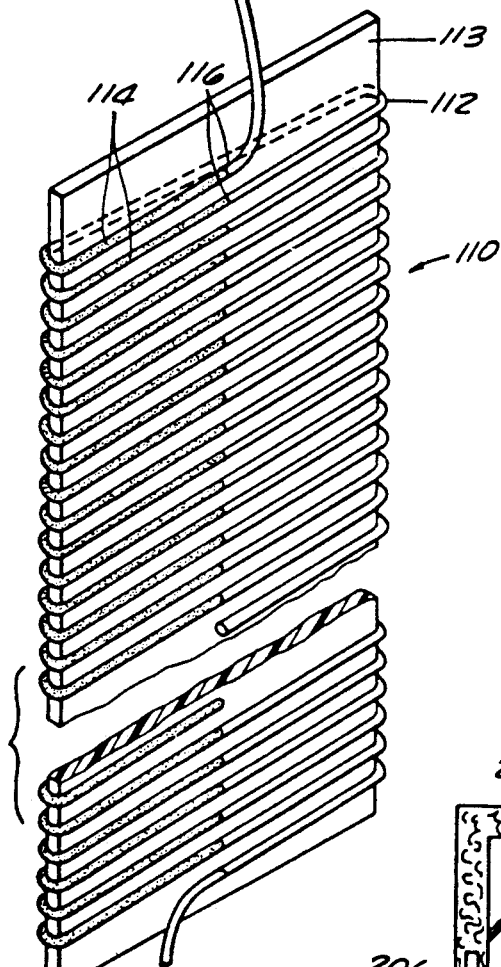
FIG. 5.
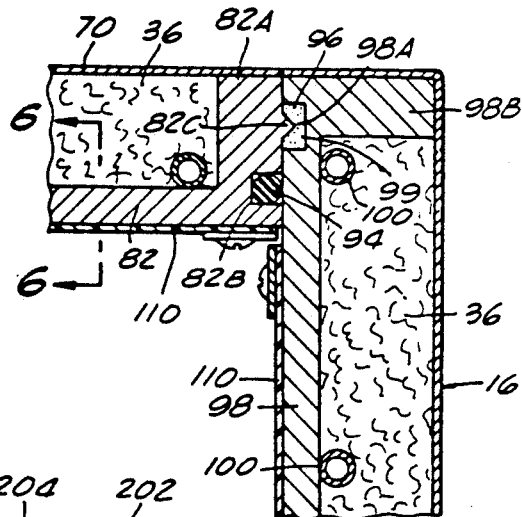
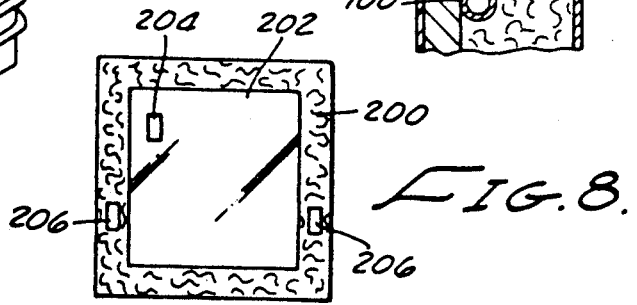
FIG. 8.
FIG. 7.

WHOLE BODY CALORIMETER

The present application is a continuation in part of my copending patent application Ser. No. 718,747 filed Apr. 1, 1985 which in turn is a continuation of my application Ser. No. 407,737 filed Aug. 13, 1982, both earlier applications having been abandoned before the patenting or abandonment of or termination of proceedings.

The present invention relates to improved means and techniques useful in the treatment and/or observation of conditions in patients, animals and other living things by measuring metabolic heat releases.

An object of the present invention is to provide an improved calorimeter for these purposes involving the concept of using good heat conducting panels for imparting structural strength and also for providing a heat sink into which substantially all the heat from a source within the calorimeter box flows after being measured by heat flow measuring means.

Another object of the present invention is to provide a calorimeter as set forth in the preceding paragraph with the addition of a transparent window together with means and techniques whereby heat losses from such window are accounted for.

Another object of the present invention is to provide an improved calorimeter of this character in which the person's or patient's head is within a transparent duct system that allows him or her to see and talk to attendants and through which there is an air flow past the person's head and neck and then into the calorimeter box.

Another object of the present invention is to provide new teachings and arrangements for accounting for heat losses through a transparent window.

Another object of the present invention is to provide an improved calorimeter of this character in which thermopile panels are mounted in a novel manner with respect to structural elements that function also as a heat sink.

Another object of the present invention is to provide an improved calorimeter of this character involving improved sealing means between the door and calorimeter box itself.

The features of the present invention which are believed to be novel are set forth with particularity in the appended claims. This invention itself, both as to its organization and manner of operation are set forth with particularity later herein with further objects and advantages thereof being best understood by reference to the following description taken in connection with the accompanying drawings in which:

FIG. 1 is a perspective view of a calorimeter embodying features of the present invention with some parts broken away for purpose of illustrating internal structure.

FIGS. 2 and 4 are sectional views taken substantially on lines 2—2 and 4—4 of FIG. 1 and FIG. 3 is a sectional view taken along a line perpendicular to line 3—3 of FIG. 2.

FIG. 5 is a sectional view taken substantially as indicated by line 5—5 in FIG. 1 with however, the door in closed position.

FIG. 6 is a sectional view taken substantially on line 6—6 of FIG. 5.

FIG. 7 is a perspective view illustrating thermopile constructions used in the calorimeter.

FIG. 8 illustrates a modification of the present invention in which a transparent window surrounded by a heat insulating frame is used to observe persons or animals inside a calorimeter and the association of heat flux sensors for accounting for heat losses through the window-insulating material combination.

Figure 1:
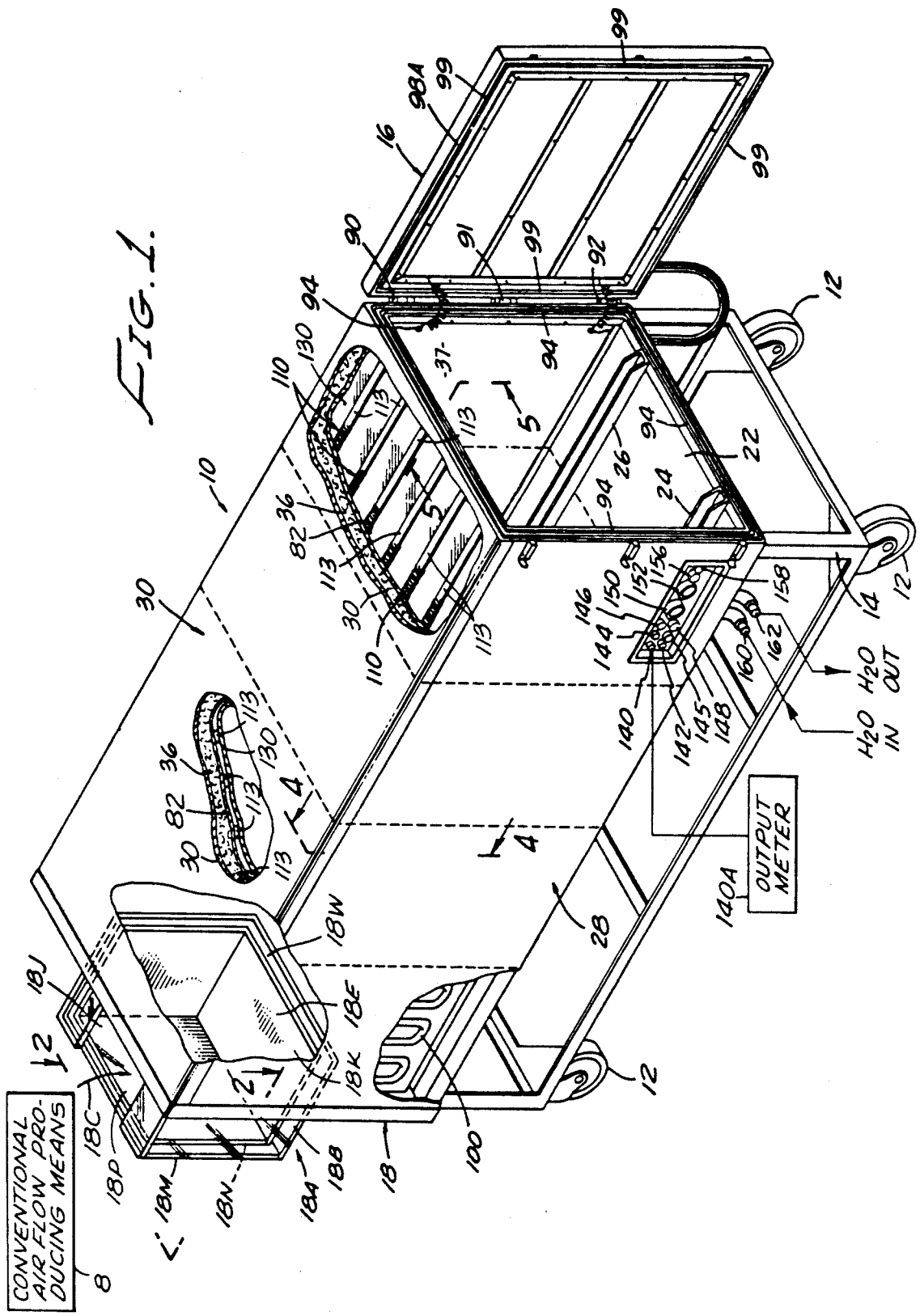

The calorimeter as illustrated is generally in the form of a rectangular box 10 sufficiently large to accommodate a human being, and it is made portable in the sense that it includes four ground engaging wheels 12 rotatably mounted on the lower end of an open rectangular framework 14 which supports the box 10 at a convenient height above the surface of the floor or ground.

Access to the interior of the box 10 is had through a hinged door 16 forming one end of the box 10, the other end of the box being closed except that it is formed with a transparent protuberance 18A in the form of a box-shaped duct system 18B into which the person's or patient's head is disposed at 18E to allow him to see and communicate with the attendants outside the box 10.

Air enters the box-shaped double wall duct system 18B and flows past the person's head and neck as indicated by arrows 18C into the interior chamber 20 of the calorimeter box where the rest of the person's body is disposed.

This box-shaped duct system 18B includes an outer transparent rectangular box 18M which is secured to wall 18 at 18H (FIG. 2), and as seen in FIGS. 1 and 2 has a top opening 18J and a side opening 18K through which ambient air may flow from the outside to the inside of box 10. Disposed within and spaced from and secured to the outer box 18M as, for example, by screws or glue is an inner transparent rectangular box 18N which like the outer box 18M has a top opening 18P. The boxes 18M and 18N are maintained in spaced relationship by a series of spaced blocks 18S (FIGS. 2 and 3). The boxes 18M, 18N thus spaced provide a double wall transparent structure which is mounted on one end of box 10 in good heat conducting relationship to heavy metal side plates 80 (FIG. 2). This good heat conducting relationship is provided by the following interconnected elements: angle member 19A, screws 19B, 19C, element 18I, metal skin material 70 and screws 132A, 19D. Air is permitted to flow in the space 18W between the spaced sides of boxes 18M, 18N from the corresponding top openings 18J, 18P. The wall of the inner box 18N adjacent opening 18K is open.

This inner box 18N within which the subject's head is disposed serves as an internal transparent shield, i.e., a radiation shield. Almost all the radiant energy from the person's head is absorbed by the walls of the inner radiation shield, i.e., inner box 18N which is removed by convection by the air flow contacting box 18N in its passage through the duct system and into the calorimeter box. Only a small fraction of the radiant heat loss from the person's head is lost through the flow opening in the transparent duct system. It is noted that the outer box 18M is exposed to the ambient air and thus has substantially the same temperature as the ambient air and consequently there is substantially no heat radiated from the ambient air to the outer box 18M.

The air flow whose presence and direction is indicated by the various arrows 18C in FIGS. 1 and 2 is generally in the following path. The air flow enters the top openings 18J, 18P of the outer and inner boxes 18M, 18N respectively and continues its flow as indicated by the various arrows 18C (FIGS. 1 an 2). The air entering the opening 18J flows through the space 18W between the two boxes 18M, 18N and then into the chamber 20. The air entering the opening 18P flows through the inner box 18N and then into the calorimeter chamber. Should such air flow, which, for example, may be produced by any of various conventional means illustrated generally in FIG. 1 as air flow producing means 8, be interrupted, i.e. become non-existent, it, of course, is no longer present and effective to carry the person's head heat releases into the chamber but the person is still able to breath ambient air without being suffocated. Applicant makes no claim for any exclusivity in any of such conventional air flow producing means 8.

The box 10 floor portion 22 has U-shaped parallel extending rail members 24, 26 are mounted for receiving and guiding the movement of wheels (not shown) of a wheeled stretcher, bed or cot (not shown) upon which a human being or other live being may rest while being within and being subjected to the environment inside the box 10 for performance of metabolic tests.

The ends, sides, floor and the rest of the box 10 are constructed to prevent heat flow therethrough to or from the room environment and to achieve that purpose, as seen in FIG. 4, the box side 28, roof 30 and floor 22 each includes heat insulating material 36. Likewise, such heat insulation material 36 as seen in FIG. 5 is included also in the door 16. The other end 18 to which the open outer box 18M is secured likewise includes insulation 36.

The outside surface of box 10 is formed in general of thin aluminum or sheet steel or skin material 70 as illustrated in FIGS. 2 and 4 except where there is a transparent air conduit means 18M, 18N at one end of the calorimeter.

Insulating material 36 is retained in pockts 36A using outwardly extending flange portions 80A (FIG. 2) of metal panels 80 and skin material 70 which together with fastening means 19D provides a means for fastening the skin material to the panels 80 to retain insulation 36 in the pockets 36A which are defined essentially by the flanged panels 80 and skin material 70.

The door 16 is as indicated in FIG. 1 hinged at 90, 91, 92 to wall 37. In the closed condition of the door, it is sealed with respect to the side walls, the roof and also to the floor, using a construction shown in FIG. 5 involving a generally rectangular elastic or "O" ring seal 94, of for example, rubber and also a so called grease seal 96.

Thus in FIG. 5 the aluminum roof portion 82 has a flanged portion 82A with a recessed portion 82B to accommodate the upper horizontal leg of the rectangular seal 94. Such flanged portion 82 also has a projecting portion 82C extending along its entire width and into a grooved portion 98A of the aluminum door panel 98 which is formed also with flanged portion 98B. This construction illustrated in FIG. 5 serves also to illustrate the manner in which the door cooperates with the two sides 28, 37 as well as the floor 22. In each of these there is a like projecting portion 82C which enters like continuous grooved portion 98A filled with sealing grease 99.

Structural strength is imparted by the wall constructions using 5/16 inch aluminum sheeting which is also used as a form of heat sink as described hereinafter. Thus in FIG. 4 the side wall 28 (typical also of the construction of the other side wall 37) includes a heavy aluminum plate 80 joined to a like aluminum floor plate 81 and ceiling plate 82. One end of plate 80 as seen in FIG. 2 has a flanged portion 80A and a recessed portion 80B in which a generally rectangular seal member 83 of, for example, rubber is disposed.

The heavy aluminum walls, roof, floor, and door panel, as indicated previously, serve in the nature of a heat sink from which heat developed inside the calorimeter is conducted away as rapidly as it reaches the aluminum. This is accomplished by maintaining the aluminum panels at a substantially constant temperature. This is done by circulating water through grids of tubing 100 of copper or other good heat conducting material which is secured to the aluminum panels in good heat conducting relationship as, for example, by soldering.

The heat flow to this form of heat sink is effectively measured and/or indicated using a plurality of thermopile sandwich panels which form the inner surfaces of the walls.

This thermopile construction 110 is illustrated in FIGS. 6 and 7 and their positions in, for example, the roof are illustrated in FIG. 1. Basically, each of the thermopiles, one of which is shown in FIG. 7 may be constantin wire 112 wrapped around a bakelite strip 113 having, for example, a thickness of 0.020 inch. This strip 113 may be of bakelite or a plastic of low thermal conductivity whose characteristics do not appreciably change. The wire 112 after wrapping may be coated along selected portions with a silver or copper coating 114 as indicated by the stripling in FIG. 7 to provide a series of hot junctions 116 along one face of the strip 113 and correspondingly, a series of cold junctions 118 (FIG. 6) is spaced along the other side of strip 113. The thermopiles thus constructed are sandwiched between the electrically insulating sheets 120, 121, such sheets 120, 121 being spaced by intervening electrically insulating sheets 114. The outer surface of these sheets 120, 121 may be clad with the copper coating or layer 126, 127 respectively. The purpose of such copper cladding is for temperature stabilization. The copper cladding is in good direct heat conducting relationship with the aluminum panel illustrated as the roof panel 82, it being understood, however, that like thermopile sandwich constructions are in good heat conducting relationship to the aluminum panels forming the structural elements of the walls, floor and door of the calorimeter box. The outer copper cladding 126 is covered with a protective sheet 130. The individual panels so constructed may be secured mechanically to the combination aluminum frame and heat sink members using screws of insulating material as, for example, nylon screws 132.

The individual thermocouples may be spaced somewhat as indicated in FIG. 1 wherein as shown in FIGS. 1 and 6 the thermopiles 110 and their mounting strips 113 lie in planes substantially parallel with the plane of the metal panel 82 and with the spacing between adjacent strips 113 being greater than the width of one of such strips and with the spacing, however, not being too large so that, in any event, the group of thermopiles serve to sense all the heat flow from the interior of the calorimeter box to the surrounding heat sink. Thermocouples or thermopiles 180 (FIG. 2) are also advantageously located continuously all the way around the rectangular opening R behind the L-shaped plastic sheet liner L which defines opening R. Here again these thermopiles 180 are in the path of heat flow from the interior of the calorimeter chamber to the heavy metal heat sink which as seen in FIG. 2 includes the flanged L-shaped heavy metal cap 181 that is secured to the heavy metal panel 80 by screws 132A. The thermopiles are connected electrically in additive relationship with all of the series connected thermopiles in the roof being connected in series with all of the thermopiles of the walls and of the floor and also of the door so that there is one electrical output in the form of a voltage or current which serves as a measure of the heat flow from the interior of the calorimeter box to the heat sink.

The output of the thermopiles appears at a jack 140 in FIG. 1. Such output may be displayed in conventional manner on a conventional output meter 140A connected to jack 140. A jack 142 having multiple conductors may have connected thereto various electrical inputs and/or outputs such as, for example, calibration circuits, power circuits. Auxillary temperature sensor circuits may be connected to the connector of jack 144. Jack 145 is an optional spare jack. Conduits may also be provided with, for example, intravenous flow connections 146, 148 for use with a patient in the calorimeter box.

Conduit connections 150, 152 are ventilating air outlets and optional air inlet connections respectively so that the heat added to such ventilating air introduced through the top opening 18J (FIG. 1) and also in some cases introduced through the inlet opening 152 together with the heat present in moisture accompanying such air may be measured and analyzed. Other conduits 156, 158 may be provided, for example, for connection to an oxygen mask system and for conducting gases expelled by a patient. Preferably all air is introduced by conventional means 8 through the top opening 18J to produce air circulation past the person's head and neck.

The two lower conduits 160 and 162 are the water inlet and outlet openings through which constsnt temperature water is circulated for purpose of maintaining the heat sink at a substantially constant temperature.

A HEAT LOSS MEASUREMENT SYSTEM FOR A CALORIMETER DOOR OR WALL CONTAINING THERMAL INSULSTION AND A THERMAL WINDOW

At times researchers using a metabolic calorimeter wish to observe the animal under study and thus a thermal window is added to the calorimeter wall or door as in this modification of the invention as described below.

In the case of a small calorimeter, it can be too difficult and expensive to cut a hole into a heat flux sensor plate that normally covers the calorimeter walls and door. Therefore, the wall or door where the window is to be inserted is made of an insulating frame, as for example foam material 200 as illustrated in FIG. 8. A thermal window 202 is fitted in the insulating frame 200. The frame 200 may be mounted in either the door or a side wall of the calorimeter described above to allow viewing of the inside of the calorimeter from the outside thereof.

In order to account for the small amount of heat loss that takes place through the insulating frame and thermal window there is provided in accordance with features of the present invention, a heat flux sensor system that will allow this smaller heat flux term to be determined.

One heat flux sensor 204 having a constant $K_w$Btu/hr ft$^2$ millivolt is placed over the thermal window 202. Several heat flux sensors 206, connected electrically in series, combined to have a combined Constant, $K_{in}$Btu/hr ft$^2$ millivolt are placed in the insulating area surrounding the window. The total heat loss from the window system is $q_t$:

$$q_t \text{ equals } q_{window} \text{ plus } q_{insulation} \quad (1)$$
$$\text{equals } (q/A)_w A_w \text{ plus } (q/A)_{in} A_{in}$$

where:
$q_{window}$ is the heat flow through the window in Btu/hr.
$q_{in}$ is the heat flow through the insulation in Btu/hr.
$(q/A)_w$ is the heat flux through the window in Btu/hr ft$^2$.
$(q/A)_{in}$ is the heat flux through the insulation in Btu/hr ft$^2$.
$A_w$ and $A_{in}$ are the window and frame insulation areas respectively ft$^2$.

The relationship between the heat flux through a heatmeter and its millivolt output signal, E, and calibration constant K is:

$$q/A \text{ equals } KE \quad (2)$$

Thus equation (1) becomes, $$q_t \text{ equals } K_w E_w A_w \text{ plus } K_{in} E_{in} A_{in} \quad (3)$$

Preferably, as in accordance with features of the present invention, the window flux sensors 206 on the insulation are connected electrically in series. In such case, in order that the millivolt signals $E_W$ and $E_{IN}$ can be meaningfully added, the following requirements must be met, $$K_W A_W \text{ equals } K_{IN} A_{IN} \quad (4)$$

or $$q_t \text{ equals } K_W A_W (E_W \text{ plus } E_{IN}) \quad (5)$$

One uses sensors with constants such that equation (4) above is satisfied.

While the particular embodiments of the present invention have been shown and described, it will be obvious to those skilled in the art that changes and modifications may be made without departing from the invention in its broader aspects and, therefore, the aim in the appended claims is to cover all such changes and modifications as fall within the true spirit and scope of this invention.

I claim as my invention:
1. In a calorimeter,
   a housing defining a hollow chamber adapted to receive substantially all of the trunk and limbs of a person for studies involving metabolic heat releases of the person;
   said housing being formed substantially of heavy metal which serves as a heat sink of substantially constant temperature for metabolic heat releases flowing from the person, when positioned in the interior of said chamber, into said heavy metal;
   and thermopile means mounted on and within said hollow chamber in the path through which said heat releases flow in their passage to the heat sink from the interior of said chamber;
   air inlet conduit means mounted on said housing into which the person's head may be disposed for allowing flow of entering ambient air from outside of said housing past the head of the person and then into said hollow chamber;
   said air inlet conduit means incorporating means for intercepting and absorbing substantially all the heat radiated from the person's head, the last mentioned means permitting transport of substantially all the radiant heat from the person's head to the flow of entering ambient air into said chamber;

insulation means mounted on said structure and insulating said structure from the ambient atmosphere;

and means connected to said thermopile means for measuring substantially all the heat releases flowing from the interior of said chamber through said thermopile means into said heat sink.

2. A calorimeter as set forth in claim 1 in which said air inlet conduit means is shaped to receive the person's head, when that person is in said hollow chamber;

said air inlet conduit means including a first wall structure thereof encompassing the person's head and including also a second outer wall structure encompassing the first wall structure;

means mounting said second wall structure in spaced relationship to said first wall structure to provide an air flow space between said first and second wall structures through which ambient air may flow from outside said chamber to the interior of said chamber;

the first wall structure being spaced from the person's head to intercept heat radiated from the person's head and to thereby serve as a heat radiation shield; and ambient air being allowed to flow in said air flow space in contact with said radiation shield and between said first wall structure and said second wall structure from the exterior of said structure and then into said hollow chamber to carry with its flow substantially all said heat radiated from the person's head onto said first wall structure into said chamber.

3. A calorimeter as set forth in claim 2 in which said double wall structure is transparent and is mounted on said heavy metal in good heat conducting relationship thereto.

4. A calorimeter as set forth in claim 1 in which said housing includes side walls, a floor, and a ceiling, said side walls, said floor, and said ceiling each including a heavy metal panel, all of which are structurally joined together to provide substantially all of the structural strength for said side walls, said floor and said ceiling of said housing.

5. A calorimeter as set forth in claim 4 in which said housing has an end wall in the form of a door, means pivoting said door on an adjacent side wall, said door being formed of a heavy metal panel and serving also as a heat sink and providing substantially all the structural strength of said door, and metal conduit means mounted directly on said metal door panel in good heat conducting relationship thereto adapted to carry a fluid of substantially constant temperature through said conduit means, and thermopile means heat conductively mounted on the interior surface of said door through which heat travels in its passage to said heat sink and then to said conduit means.

6. A calorimeter as set forth in claim 5 in which heat seal means is disposed in a closed rectangular pattern between said door and all adjacent ends of said door, walls and ceiling to provide a sealed end of said chamber.

7. A calorimeter as set forth in claim 6 in which said heat seal means includes a groove in said door, grease in said groove and protrusion means on said ends of said door, walls and ceiling for extending into said grease.

8. a calorimeter as set forth in claim 5, said metal panels having outwardly extending flange portions which define pockets for retention of some of said insulation means, said insulation means being in said pockets, an outer thin covering sheet extending over said flange portions and said insulation means, said flange portions defining means for fastening the outer thin covering sheet over said insulation means to retain it in said pockets, and means for fastening said covering sheet to said flange portions.

9. A calorimeter as set forth in claim 8 in which said thermopile means means includes hot and cold junctions, strips of insulating material on opposite sides of which said hot and cold junctions are disposed, and said strips lie in planes substantially parallel with the plane of said metal panels with spacing between adjacent strips being greater than the width of one of said strips.

10. A calorimeter as set forth in claim 9 including insulating sheets which are spaced from each other, said strips being maintained in said space defined between said sheets, each of said sheets having a thickness greater than the overall thickness of said thermopiles.

11. A calorimeter as set forth in claim 1 including a transparent window, means mounting said window on said housing, said window allowing a person outside said housing to view the interior of said chamber, said mounting means including a heat insulating frame mounted on said housing in contact with said window and surrounding said window, at least one heat flux sensor means on said window for sensing the flow of heat therethrough in terms of an electrical output signal thereof, a plurality of heat flux sensor means mounted on said insulating frame for sensing the flow of heat therethrough in terms of an electrical output signal thereof, said sensor means on said window and said sensor means on said insulating frame being electrically serially connected and satisfying the following relationships: $K_w A_w$ equals $K_{in} A_{in}$ where $A_w$ and $A_{in}$ are respectively the area of said window and the area of said frame and $K_w$ and $K_{in}$ are respectively the calibration constant of the window sensor means and the combined calibration constant of the insulating frame sensor means and where the calibration constant $K_w$ is equal to the heat flux through the sensor means on the window divided by the corresponding signal output, and the calibration constant $K_{in}$ is equal to the heat flux through the sensor means on the insulating frame divided by the corresponding combined signal output produced by said heat flux through said sensor means on said insulating frame.

* * * * *